(12) United States Patent
Van Westrenen et al.

(10) Patent No.: US 8,269,056 B2
(45) Date of Patent: Sep. 18, 2012

(54) PROCESS FOR THE PREPARATION OF AN OLEFINIC PRODUCT

(75) Inventors: Jeroen Van Westrenen, Amsterdam (NL); Leslie Andrew Chewter, Amsterdam (NL); Ferry Winter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 81 days.

(21) Appl. No.: 12/743,273

(22) PCT Filed: Nov. 19, 2008

(86) PCT No.: PCT/EP2008/065863
§ 371 (c)(1),
(2), (4) Date: Jun. 25, 2010

(87) PCT Pub. No.: WO2009/065870
PCT Pub. Date: May 28, 2009

(65) Prior Publication Data
US 2010/0261943 A1   Oct. 14, 2010

(30) Foreign Application Priority Data

| Nov. 19, 2007 | (EP) | 07120962 |
| Nov. 19, 2007 | (EP) | 07120963 |
| Nov. 19, 2007 | (EP) | 07121003 |
| Nov. 19, 2007 | (EP) | 07121005 |
| Nov. 19, 2007 | (EP) | 07121008 |
| Nov. 19, 2007 | (EP) | 07121014 |

(51) Int. Cl.
*C07C 1/00* (2006.01)

(52) U.S. Cl. .......... 585/639; 585/638; 585/640

(58) Field of Classification Search .......... 585/638, 585/639, 640, 809; 526/67, 75, 194
See application file for complete search history.

(56) References Cited

U.S. PATENT DOCUMENTS

| 4,076,796 A | 2/1978 | Reh et al. | 423/659 |
| 4,076,842 A | 2/1978 | Plank et al. | 423/328 |
| 4,397,827 A | 8/1983 | Chu | 423/326 |
| 4,556,477 A | 12/1985 | Dwyer | 208/111 |
| 4,590,320 A | 5/1986 | Sapre | 585/324 |
| 4,665,249 A | 5/1987 | Mao et al. | 585/408 |
| 5,367,100 A | 11/1994 | Gongwei et al. | 585/640 |

(Continued)

FOREIGN PATENT DOCUMENTS
DE   10027159   12/2001
(Continued)

OTHER PUBLICATIONS

Weissermehl, K., et al: Industrial Organic Chemistry, $3^{rd}$ Edition, Wiley, 1997, pp. 13-28.

(Continued)

*Primary Examiner* — Tam M Nguyen

(57) ABSTRACT

Process for the preparation of an olefinic product, which process comprises contacting a reaction mixture comprising an oxygenate feedstock and an olefinic component with an oxygenate conversion catalyst comprising a molecular sieve having one-dimensional 10-membered ring channels, in a flow-through reactor unit defining a flow trajectory for fluids towards a downstream outlet for an olefinic reaction effluent from the flow-through reactor unit, wherein an olefinic co-feed is added at an upstream olefin feed inlet of the flow-through reactor unit, and wherein oxygenate feedstock is admitted to the reactor such that it is added to the reaction mixture at a plurality of locations along the feed trajectory.

14 Claims, 6 Drawing Sheets

U.S. PATENT DOCUMENTS

| | | | |
|---|---|---|---|
| 5,817,906 A | 10/1998 | Marker et al. | 585/640 |
| 6,046,372 A | 4/2000 | Brown et al. | 585/640 |
| 6,791,002 B1 | 9/2004 | Abrevaya et al. | 585/648 |
| 6,797,851 B2 | 9/2004 | Martens et al. | 585/640 |
| 6,987,152 B1 * | 1/2006 | Eisinger et al. | 526/77 |
| 7,151,198 B2 * | 12/2006 | Van Egmond | 585/327 |
| 2002/0115898 A1 * | 8/2002 | Searle | 585/639 |
| 2003/0078463 A1 | 4/2003 | Martens et al. | 585/638 |
| 2003/0088136 A1 * | 5/2003 | Lumgair et al. | 585/640 |
| 2004/0127763 A1 * | 7/2004 | Van Egmond et al. | 585/639 |
| 2006/0020155 A1 | 1/2006 | Beech, Jr. et al. | 585/639 |
| 2006/0135834 A1 | 6/2006 | Xu et al. | 585/639 |
| 2007/0197844 A1 * | 8/2007 | Beech et al. | 585/638 |
| 2007/0276171 A9 * | 11/2007 | Iaccino et al. | 585/407 |
| 2009/0105429 A1 | 4/2009 | Chewter et al. | 526/67 |
| 2011/0295049 A1 * | 12/2011 | Chewter et al. | 585/638 |
| 2011/0306814 A1 * | 12/2011 | Chewter et al. | 585/638 |

FOREIGN PATENT DOCUMENTS

| | | |
|---|---|---|
| DE | 10043644 | 3/2002 |
| EP | 88494 | 9/1983 |
| EP | 340576 | 11/1989 |
| EP | 343454 | 11/1989 |
| EP | 485145 | 5/1992 |
| EP | 489497 | 6/1992 |
| WO | WO9522516 | 8/1995 |
| WO | WO0162689 | 8/2001 |
| WO | WO0185872 | 11/2001 |
| WO | WO03020667 | 3/2003 |
| WO | WO2004018089 | 3/2004 |
| WO | WO2004031327 | 4/2004 |
| WO | WO2004037950 | 5/2004 |
| WO | WO2004056944 | 7/2004 |
| WO | WO2006020083 | 2/2006 |
| WO | WO2007135052 | 11/2007 |

OTHER PUBLICATIONS

Ch. Baerlocher, et al: Database of Zeolite Structures: http://www.iza-structure.org/databases/-.

* cited by examiner

PROCESS FOR THE PREPARATION OF AN OLEFINIC PRODUCT

PRIORITY CLAIM

The present application claims priority to European Patent Application 07121005.8 filed 19 Nov. 2007; European Patent Application 07121003.3 filed 19 Nov. 2007; European Patent Application 07121014.0 filed 19 Nov. 2007; European Patent Application 07121008.2 filed 19 Nov. 2007; European Patent Application 07120962.1 filed 19 Nov. 2007 and European Patent Application 07120963.9 filed 19 Nov. 2007.

FIELD OF THE INVENTION

This invention relates to a process for the preparation of an olefinic product, in particular including lower olefins such as ethene and/or propene, more in particular for maximizing selectivity of the process towards ethylene. More in particular this invention relates to a process for the conversion of an oxygenate feedstock into olefins, in particular including lower olefins.

BACKGROUND OF THE INVENTION

WO-A-01/62689 describes a process for converting oxygenate to an olefin-containing product wherein oxygenate is introduced into a reactor system at plural stages along a flow axis of a reactor catalyst bed. For reactions of methanol over ZSM-34, SAPO-34, and of methanol with toluene over ZSM-5 catalysts, in a fluid-bed reactor it was shown, that ethylene selectivity improved when multiple feed injectors were used.

However, in the known process, improved selectivity is accompanied by a lower methanol conversion. In the experiments with ZSM-34 in Example 1, a significant amount of methanol remained unconverted. Also for SAPO-34, a decreasing conversion with increasing number of injectors is found. In the known process conversion of oxygenate is therefore already a problem at the relatively low reaction temperatures of between 375-470° C. In view of the lower conversion it is proposed to increase the catalyst activity, or to allow a lower conversion, optionally followed by a recycle of unreacted oxygenate. Increasing the reaction temperature is not an option, as this increases the deactivation of the catalyst.

There is a need for an improved process for the conversion of oxygenate to olefin in which the selectivity towards desired olefin species, in particular ethylene, can be increased while providing sufficient activity and stability so that high oxygenate conversion can be realized in an industrial-scale process.

SUMMARY OF THE INVENTION

The present invention provides a process for the preparation of an olefinic product, which process comprises contacting a reaction mixture comprising an oxygenate feedstock and an olefinic component with an oxygenate conversion catalyst comprising a molecular sieve having one-dimensional 10-membered ring channels, in a flow-through reactor unit defining a flow trajectory for fluids towards a downstream outlet for an olefinic reaction effluent from the flow-through reactor unit, wherein an olefinic co-feed is added at an upstream olefin feed inlet of the flow-through reactor unit, and wherein oxygenate feedstock is admitted to the reactor such that it is added to the reaction mixture at a plurality of locations along the feed trajectory.

DETAILED DESCRIPTION OF THE INVENTION

Figure 1:
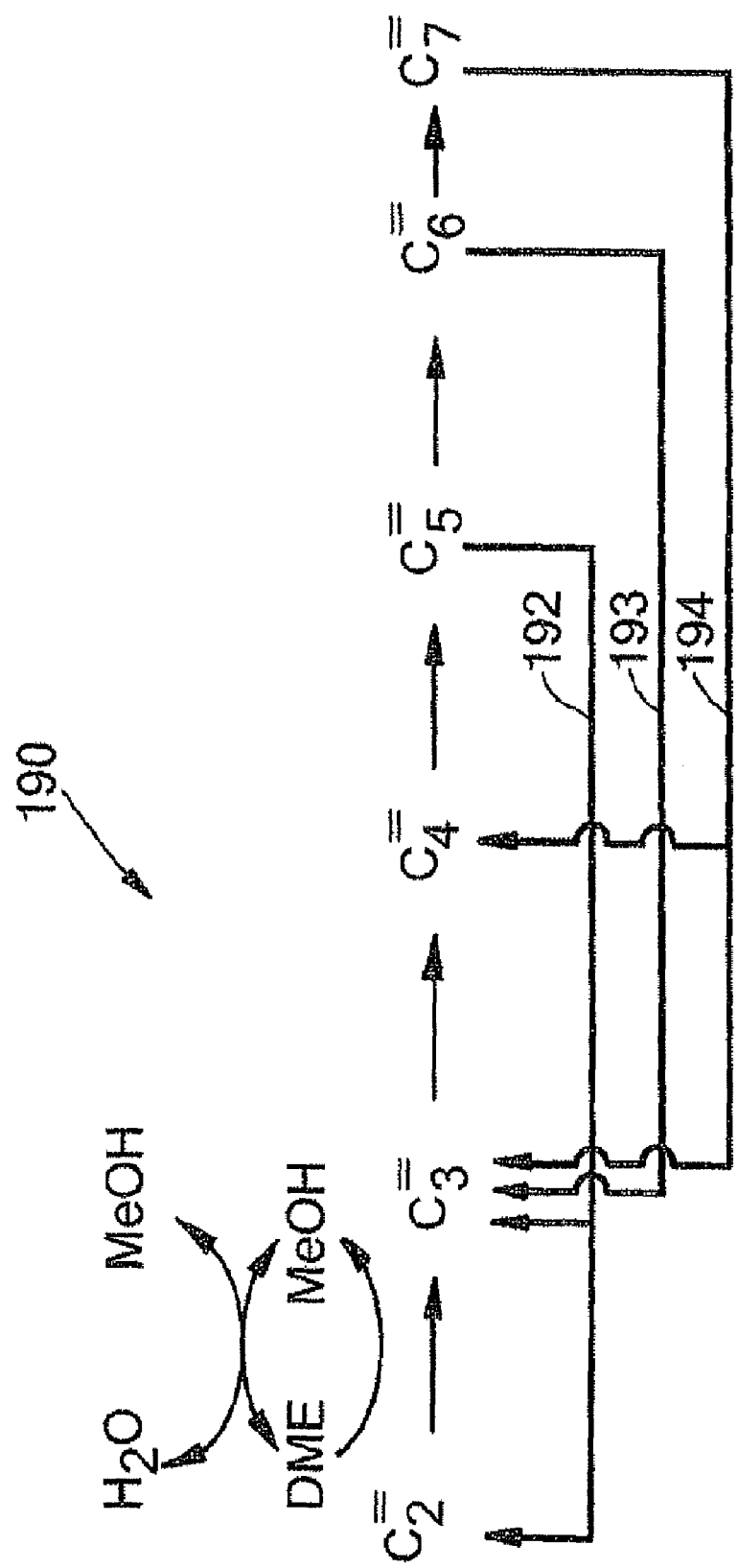
FIG. 1 schematically shows a reaction network.

The process of the invention allows optimizing the selectivity of the oxygenate conversion reaction in a molecular sieve having one-dimensional 10-membered ring channels for selected olefins. It has been found that an oxygenate conversion catalyst comprising such molecular sieve is particularly effective for converting an oxygenate feedstock, such as methanol and/or dimethylether together with an olefinic co-feed into light olefins, in particular ethylene and/or propylene.

Without wishing to be bound by a particular hypothesis or theory, applicant presently believes that in a molecular sieve having one-dimensional 10-ring channels, such as MTT type molecular sieves and/or TON type molecular sieves, alkylation of olefins and subsequent cracking occurs in a favourable fashion leading to low production of by-products such as aromatics, saturates, C5+ hydrocarbon species, methane, carbon oxides, and rather to a high yield of light olefins. For example it is currently believed that high ethylene selectivity can be obtained from a methanol and/or dimethylether feed and a C4 olefinic co-feed, wherein an optimum reaction pathway includes alkylation of the C4 olefin by the oxygenate's methyl group, followed by cracking of the resulting C5 olefin into ethylene and propylene molecules.

Applicant has realized that in this example ethylene selectivity can be increased by operating at low oxygenate concentration or partial pressure in the reaction mixture. This will prevent further alkylation of a C5 olefin, which would result in less ethylene cracking products.

Molecular sieves having one-dimensional 10-ring channels, such as MTT-type (zeolite ZSM-23) or TON-type (zeolite ZSM-22) materials can be operated at significantly higher temperatures than e.g. SAPO-34, which allows high conversion with acceptable deactivation behaviour. Preferably the reaction mixture of oxygenate and olefinic component is contacted with the oxygenate conversion catalyst to react at a temperature of more than 470° C., preferably at a temperature of 480° C. or higher, more preferably at a temperature of 490° C. or higher.

In one embodiment, an oxygenate-to-olefin ratio is kept below a predetermined threshold for a selected position along the flow trajectory, which threshold is lower than for the case that all oxygenate would be admitted at the upstream feed inlet. The oxygenate-to-olefin ratio can be related to a molar ratio of oxygen-bonded alkyl groups to olefin double bonds, in particular to a molar ratio of oxygen-bonded alkyl groups to a selected olefin species. A particular example is the molar ratio of oxygen-bonded methyl groups to C5 olefins, and it is desirable to keep this ratio low for increased ethylene selectivity. It will be understood that for example a weight ratio, volumetric ratio or partial pressure ratio could be used as well, which are all directly related to the molar ratio.

In one embodiment the oxygenate conversion catalyst flows through the reactor as well, and oxygenate conversion catalyst is admitted to the reactor at multiple locations along the flow trajectory. Suitably oxygenate conversion catalyst is admitted at substantially the same locations as oxygenate feedstock. In this way the weight hourly space velocity (WHSV), defined as the throughput of the weight of reactants and reaction products per hour, and per weight of catalyst in the reactor, can be maintained above a selected minimum value, in order to achieve sufficient conversion.

In particular the cross-sectional area of the flow-through reactor system can increase in the direction of flow, i.e. between the upstream feed inlet and the downstream outlet. The increase can take place in one or more steps, but also more or less continuously. The increasing cross-sectional area preferably takes place there where additional oxygenate catalyst is added. Increasing the cross-sectional area can partly or fully compensate for the increase in volumetric flow rate due to additional feedstock and/or catalyst, so that the flow velocity in the reactor does not increase beyond critical values impeding for example conversion, catalyst stability and/or attrition.

In one embodiment the flow-through reactor comprises a plurality of sequential reaction zones, which can be in one reactor vessel or in separate reactor vessels.

By sequentially (or serially) arranged is understood that at least part of the effluent of a preceding reaction zone or reactor is fed into a subsequent reaction zone or reactor, which subsequent reaction zone or reactor is in fluid communication or connected directly or indirectly with the first reaction zone or reactor. Having separate reaction zones allows easy admission of oxygenate along the flow trajectory through the reactor, e.g. at the upstream side of the reaction zones.

In one embodiment the flow-through reactor unit comprises a riser reactor, preferably a plurality of sequential riser reactor stages. This allows an efficient design of the reactor unit. Staged feeding of oxygenate and optionally oxygenate conversion catalyst can be done at the inlets to the various riser reactor stages. By increasing the cross section of subsequent riser stages the increased volumetric flow can easily be accommodated. Riser reactors allow efficient handling of catalyst deactivation by regeneration and recycling, adapted to the deactivation properties of the catalyst.

By a riser reactor is understood an upright, such as essentially vertical, reactor where a feed or feed mixture can be added at the lower end of the reactor, together with a catalyst, and an effluent comprising reaction product and catalyst can be obtained at the top of the reactor. The catalyst is typically fluidised, and the flow velocity in the riser is higher than the minimum fluidization velocity of the catalyst particles.

In a further embodiment the flow-through reactor unit comprises a fluidized bed reactor. In such an embodiment, the oxygenate feedstock is allowed to enter the reactor system at an upstream oxygenate inlet, and with such flow properties that oxygenate feedstock containing bubbles progress along the flow trajectory. In this way oxygenate is added to the reaction mixture by exchange and/or diffusion along the way. Thus, although oxygenate feedstock is present in the reactor, as long as it is present in the bubbles it does not form part of the reaction mixture surrounding and interacting with the catalyst. Only when oxygenate migrates out of the bubbles such as by diffusion or exchange with the surrounding reaction mixture, it can take part in the reaction. The concentration of oxygenate in the reaction mixture is therefore kept low along the flow trajectory.

In a particular embodiment at least part of the olefinic feedstock is obtained from recycling part of the olefin-containing product.

Figure 2:
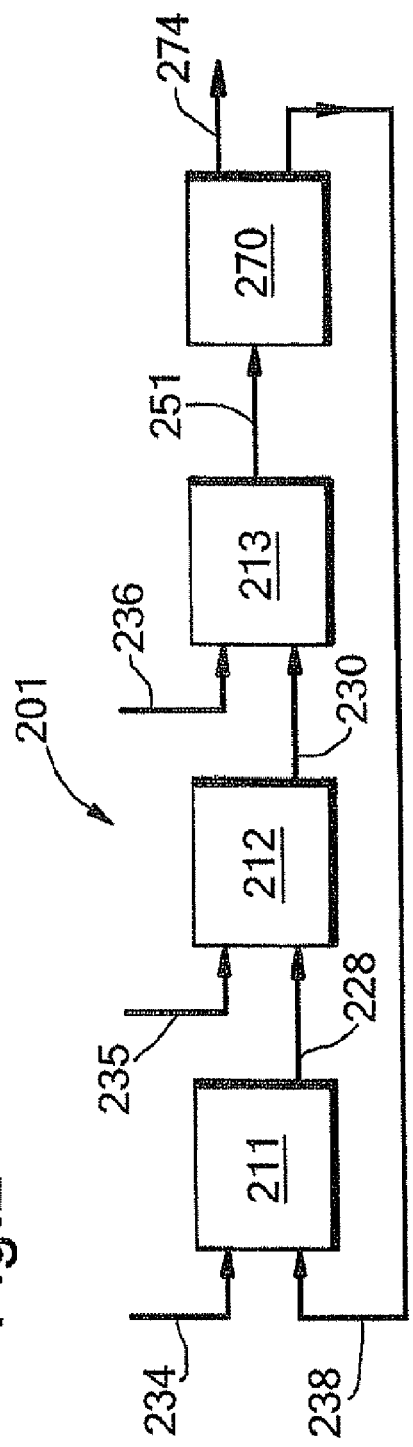
FIG. 2 schematically shows a first reactor system used in model calculations.
Figure 3:
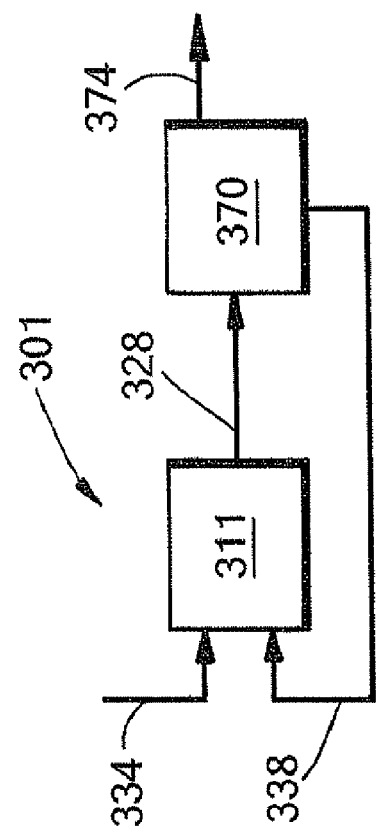
FIG. 3 schematically shows a second reactor system used in model calculations.
Figure 4:
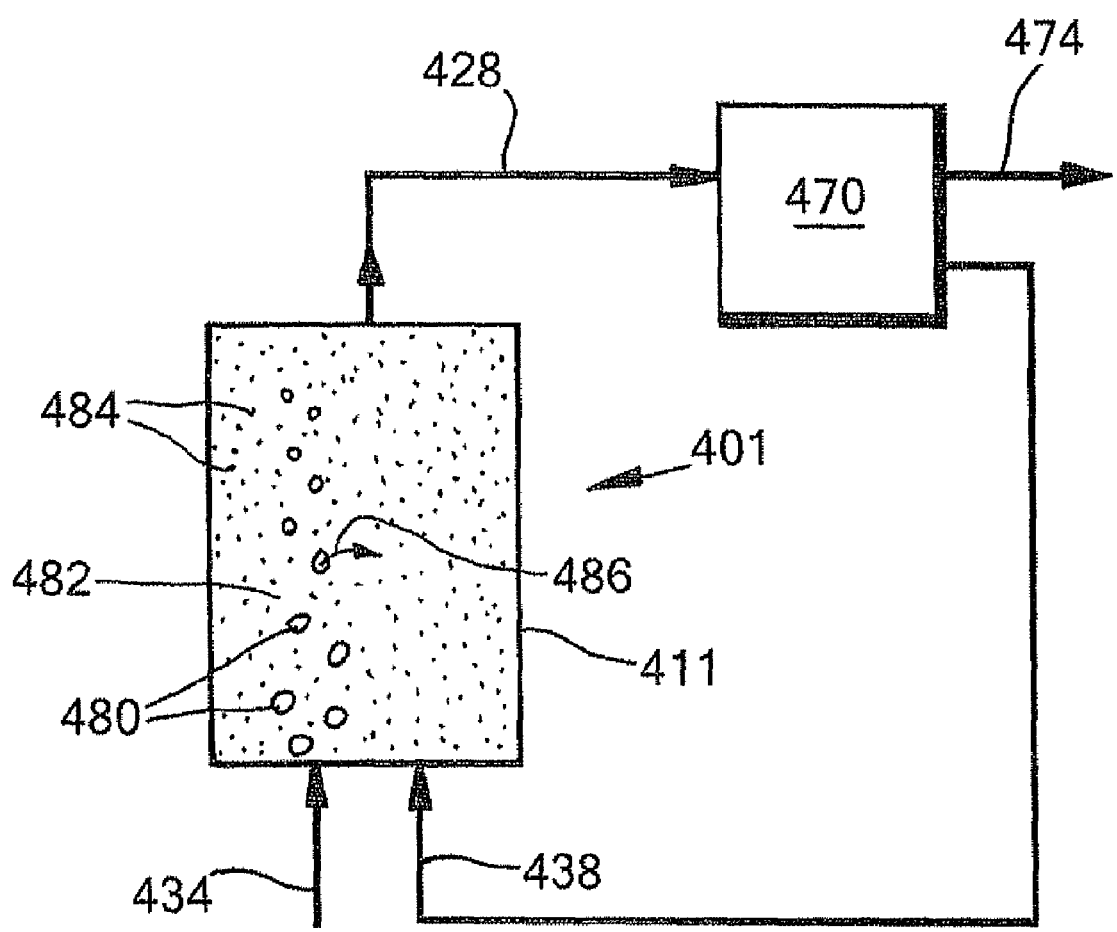
FIG. 4 schematically shows a third reactor system used in model calculations.
Figure 5:
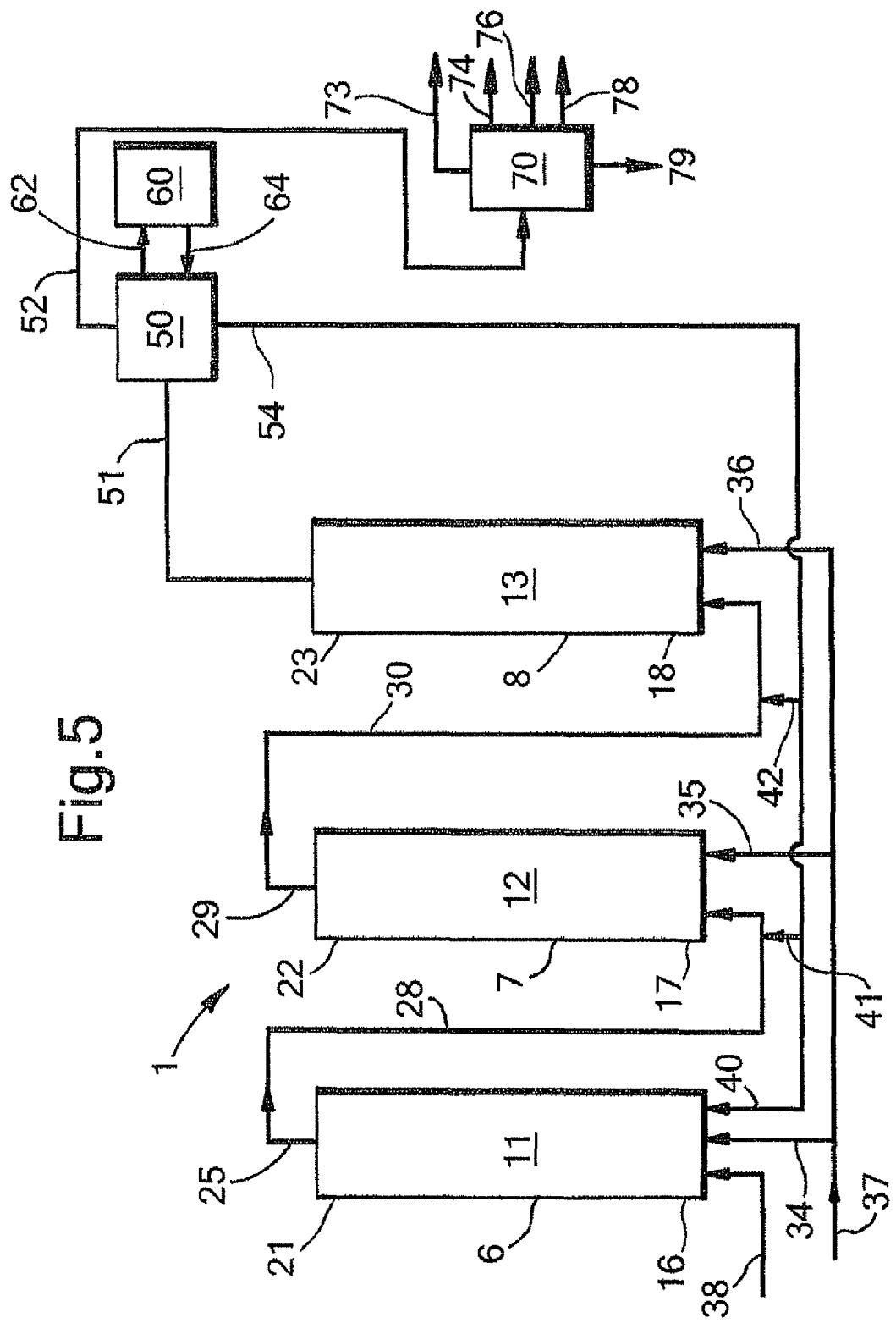
FIG. 5 schematically shows a first embodiment of a serial riser reactor system for use in the present invention.
Figure 6:
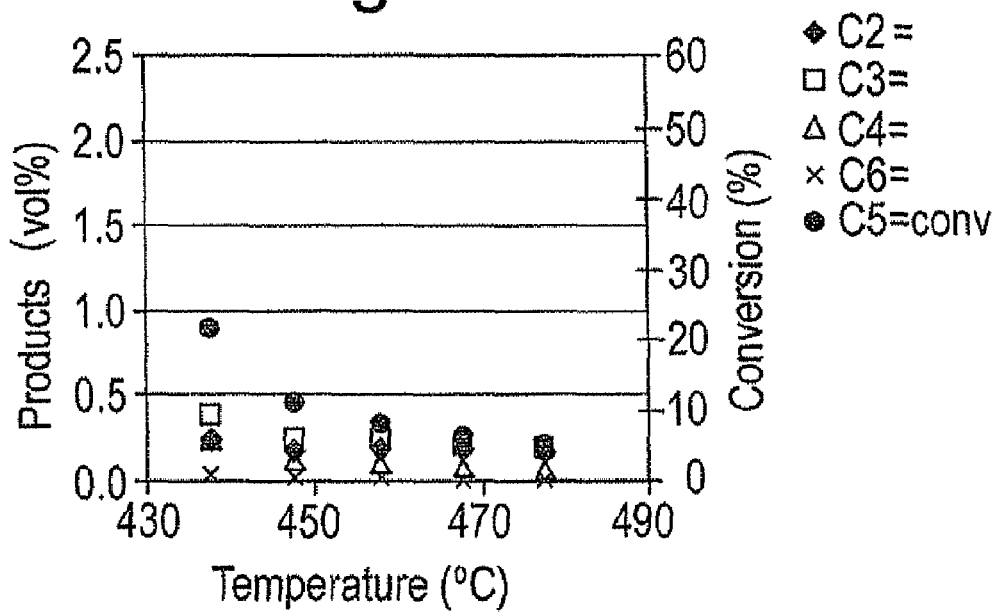
FIGS. 6 and 7 show experimental results of product distribution from C5= cracking experiments over SAPO-34 and ZSM-23, respectively, at various temperatures.
Figure 7:
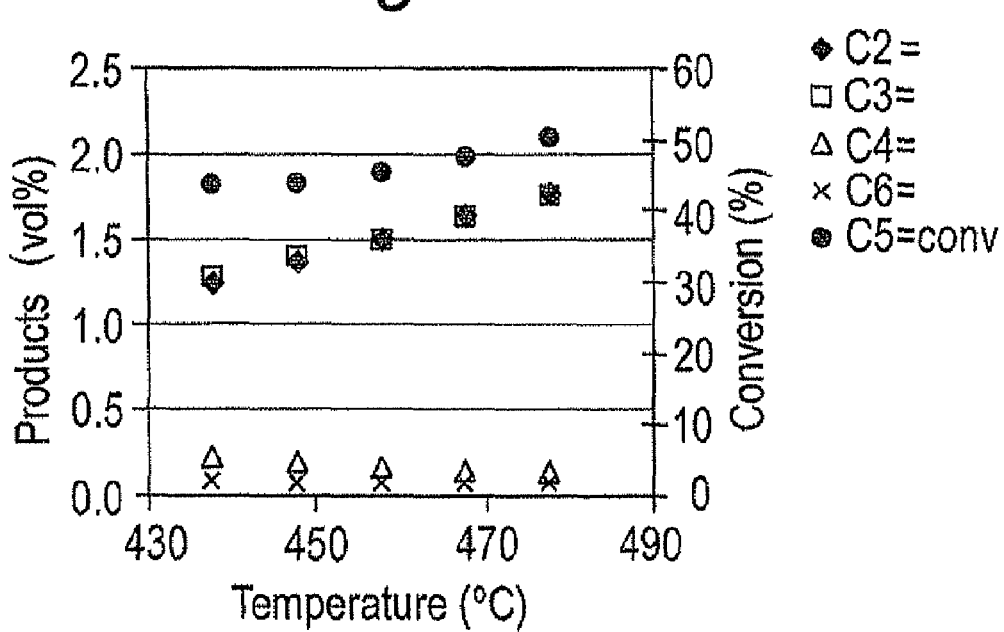
Figure 9:
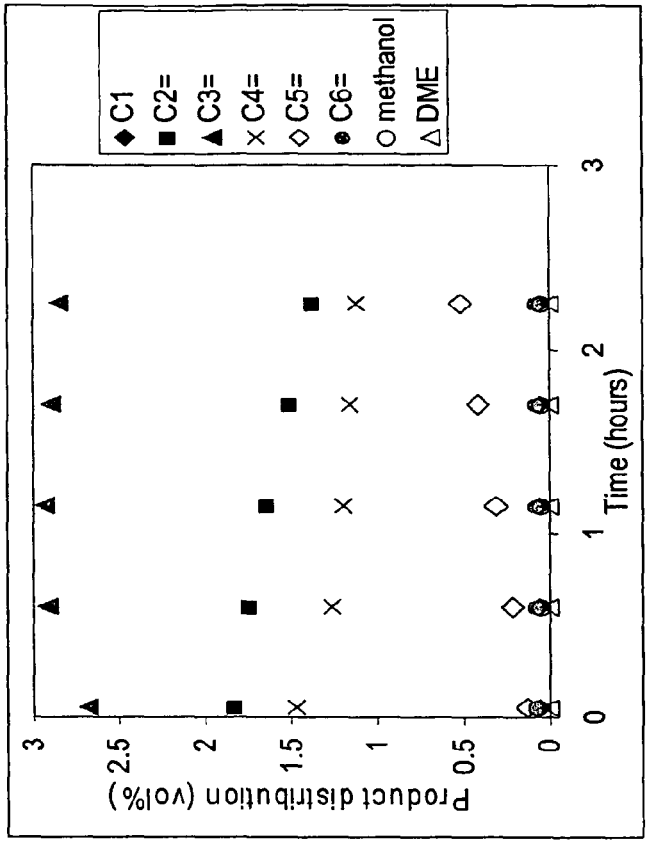
FIGS. 8 and 9 show experimental results of product distributions from converting an oxygenate feedstock and an olefinic co-feed to an olefinic product over SAPO-34 and ZSM-23, respectively, at various times on stream.
Figure 8:
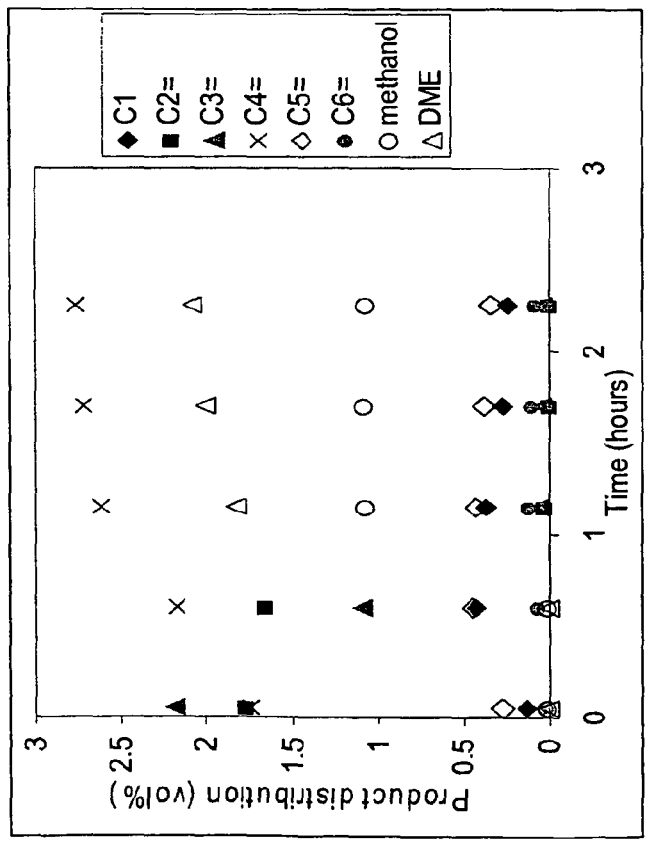

The invention will be explained in more detail and by way of example with reference to the drawings, wherein FIG. 1 schematically shows a reaction network;

FIG. 2 schematically shows a first reactor system used in model calculations;

FIG. 3 schematically shows a second reactor system used in model calculations;

FIG. 4 schematically shows a third reactor system used in model calculations;

FIG. 5 schematically shows a first embodiment of a serial riser reactor system for use in the present invention;

FIGS. 6 and 7 show experimental results of product distribution from C5= cracking experiments over SAPO-34 and ZSM-23, respectively, at various temperatures; and FIGS. 8 and 9 show experimental results of product distributions from converting an oxygenate feedstock and an olefinic co-feed to an olefinic product over SAPO-34 and ZSM-23, respectively, at various times on stream.

The process of the present invention enables the conversion of the oxygenate feed to olefins over a molecular sieve having one-dimensional 10-membered ring channels with high selectivity and conversion, which may otherwise be cumbersome. Such is illustrated in table 2B of EP-A 0485145 where it is shown that one-dimensional molecular sieves having 10-membered ring channels, such as zeolites of the TON-type, are not capable of converting an oxygenate at a reasonable rate in the absence of any olefin. Even when a mixture of methanol and n-butene is used, this document teaches that ethylene and propylene are only formed in minor amounts; the majority of the reaction product are C4+ hydrocarbons.

The olefin-containing product advantageously is a product containing lower olefins, in particular containing ethylene and/or propylene, more in particular the olefin-containing product contains at least 50 mol %, in particular at least 50 wt %, lower olefins (ethylene and propylene), based on total hydrocarbon product from the reaction. When a recycle of part of the product is used, the recycle stream is preferably not counted as olefin-containing product from the process. In a preferred embodiment the invention relates to a process for converting an oxygenate into an olefin-containing product with increased ethylene selectivity, i.e. with an increased ethylene/propylene ratio in the reaction product, in particular with a molar ethylene/propylene ratio of at least 0.5, such as of from 0.5 to 1.5.

Reference is made to FIG. 1, showing a specific example of a reaction network for conversion of oxygenate in the presence of an olefinic co-feed to olefins, at the hand of which principles underlying the present invention will be discussed. The kinetic reaction network 190 depicted in FIG. 1 represents the alkylation and cracking of C2-C7 olefins, in the presence of oxygenates comprising dimethylether (DME) and/or methanol (MeOH). Without wishing to be bound by a particular theory or hypothesis, it is presently believed that this reaction network is a useful model representation of a conversion of methanol to light olefins ethylene and propylene in a molecular sieve comprising one-dimensional 10-membered ring channels.

The reaction conditions are such that higher than C7 olefins are hardly formed and can be neglected. In the alkylation it is assumed that DME reacts with an olefin, producing methanol, and that 2 methanol molecules are dehydrated to DME. Water is being obtained as a reaction product from alkylation. This cycle is indicated in FIG. 1 for the alkylation from ethylene to propylene, and it shall be clear that it also applies to the alkylation steps of C3= and higher olefins. C2-C4 olefins are not cracked under the prevailing operating conditions. Cracking of one C5= molecule results in one C2= and one C3= molecule, cracking of C6= in two C3= molecules, and cracking of C7= in one C3= and one C4= molecule. This is illustrated by the arrows 192, 193, 194. C2 olefins and optionally C3 olefins can be withdrawn as product, and in a preferred embodiment C4 olefins are recycled to the process, optionally together with a portion of even all of the C3 olefins, so that in an especially preferred embodiment no external olefinic co-feed is required during normal operation.

At the hand of this example it is illustrated that a high concentration of oxygenate favours the alkylation reaction, leading to a more complex reaction product, the cracking of which will lead to a larger variety of species. It is therefore thought to be beneficial for selectivity towards a specific olefinic product, such as for high ethylene selectivity, if the concentration of oxygenate feedstock in the reaction mixture coming in contact with the oxygenate conversion catalyst is kept low.

According to the invention this is achieved by admitting the oxygenate feedstock to the reactor such that it is added to the reaction mixture at a plurality of locations along the feed trajectory.

On the basis of the reaction network 190 a kinetic model was established, and parameters of the model were determined based on experiments of oxygenate (DME and/or MeOH) and various olefin feed conversions over zeolite ZSM-23. The kinetic model was then used in various reactor models as discussed below. Aspen Custom Modeller was used in this process, together with proprietary software routines.

The model does not take into account the production or conversion of paraffins. It is known that some paraffins are being formed over a zeolite catalyst. One of the options of practical interest is the recycle of C4= olefins from the reaction product to the inlet of the reactor system. It is known that separating C4 olefins from C4 paraffins is difficult, and may not be economically attractive. Therefore the recycle stream may contain C4 paraffins (C4,0) together with C4=. In some Examples below, the role of C4 paraffins has been included. In order to mimic their production in the process, a small amount was included in the oxygenate feed, and a corresponding bleed stream was taken out of the product fraction. The net effect is a level of C4,0 in the process, which is further assumed to be inert.

EXAMPLE 1

Model calculations for a reactor system 201 comprising three sequential isothermal plug flow reactors have been conducted. The reactor system 201 is depicted in FIG. 2, comprising three sequential isothermal reactors 211,212,213, in fluid communication via lines 228 and 230. The three reactors can also be regarded as reaction zones and can be arranged in a single reactor vessel. In the calculations, oxygenate feedstock (DME, MeOH) was fed via lines 234,235,236, and in this way it was added to the reaction mixture at a plurality of locations along the feed trajectory. C4 olefin was fed to the first reactor 211 via line 238. Products (ethylene, propylene and water) are withdrawn after separation of C4 olefins from the olefinic effluent in line 251 in separation system 270, as generally depicted by line 274. The majority of C4=, together with C4,0, is recycled to the first reactor 211 via line 238. The flow trajectory through the flow-through reactor system 201 extends at least from the inlet end of reactor 211 to the outlet end of reactor 213.

The catalyst amount assumed in the model was 5, 7.5 and 12.5 tonnes for the reactors 211, 212, 213, respectively. 40 wt % of the catalyst was assumed to be zeolite. A uniform temperature of 522° C. and pressure of 1 bar was assumed. In an isothermal model it is not needed to consider the actual flow of catalyst through the system, therefore no catalyst separation and addition is shown.

The composition of various streams indicated by the reference numerals of FIG. 5 are given in Table 1.

TABLE 1

| | Stream (kmol/h) | | | | | | |
|---|---|---|---|---|---|---|---|
| | 238 | 234 | 228 | 235 | 230 | 236 | 251 |
| DME | 0 | 922 | 0 | 922 | 0 | 922 | 0 |
| MeOH | 0 | 326 | 0 | 326 | 1 | 326 | 1 |
| $H_2O$ | 0 | | 1248 | | 2495 | | 3743 |
| $C_2=$ | 0 | | 355 | | 794 | | 1194 |
| $C_3=$ | 0 | | 985 | | 1134 | | 1309 |
| $C_4=$ | 806 | | 426 | | 630 | | 849 |
| $C_4^0$ | 418 | 22 | 440 | | 440 | | 440 |
| $C_5=$ | 0 | | 6 | | 11 | | 5 |
| $C_6=$ | 0 | | 0 | | 0 | | 0 |
| $C_7=$ | 0 | | 0 | | 0 | | 0 |
| Total | 1224 | 1270 | 3459 | 1248 | 5505 | 1248 | 7540 |
| Total (t/h) | 69 | 54 | 124 | 53 | 176 | 53 | 229 |

A high selectivity for ethylene is observed in this staged reactor line-up, the molar ratio of C2=/C3= obtained is 0.91.

COMPARATIVE EXAMPLE 2

Model calculations for a reactor system 301 comprising a single isothermal plug flow reactor have been conducted for comparison. The reactor system 301 is depicted in FIG. 3, comprising a single isothermal reactor 311, a single oxygenate feed line 334, not according to the invention, and C4 olefin fed feed/recycle line 338. Products (ethylene, propylene and water) are withdrawn after separation of C4 olefins from the reactor effluent 328 in separation system 370, as generally depicted by line 374. The majority of C4= and C4,0 is recycled.

The catalyst amount assumed was 12.5 tonnes for the reactors 311, 40 wt % of which being zeolite. A uniform temperature of 522° C. and pressure of 1 bar was assumed.

The composition of various streams indicated by the reference numerals of FIG. 3 are given in Table 2.

TABLE 2

| Stream (kmol/h) | Recycle 338 | Feed 334 | Products 328 |
|---|---|---|---|
| DME | | 2766 | 0 |
| MeOH | | 978 | 1 |
| $H_2O$ | | | 3743 |
| $C_2^=$ | | | 674 |
| $C_3^=$ | | | 1646 |
| $C_4^=$ | 897 | | 944 |
| $C_4^0$ | 418 | 22 | 440 |
| $C_5^=$ | | | 7 |
| $C_6^=$ | | | 0 |
| $C_7^=$ | | | 0 |
| Total | 1315 | 3766 | 7455 |
| Total (t/h) | 74 | 160 | 234 |

A much lower ethylene selectivity than in the staged reactor system of Example 1 is observed. The C2=/C3= molar ratio in the product is only 0.41.

EXAMPLE 3

Model calculations were conducted for a further reactor system 401, according to the invention, comprising a fluidised bed reactor. In FIG. 4, the fluidised bed reactor 411 has a single oxygenate feed line 434, and C4 olefin feed/recycle line 438. Products (ethylene, propylene and water) are withdrawn after separation of C4 olefins from the olefinic effluent from line 428 in separation system 470, as generally depicted by line 474. C4= is recycled.

The oxygenate feedstock is injected into the fluidised bed reactor such that oxygenate containing bubbles 480 are formed, rising upwards along the flow trajectory through the reactor 411. While oxygenate is still in the bubbles, it does not form part of the reaction mixture 482 that surrounds and comes in contact with the oxygenate conversion catalyst 484. Only when oxygenate moves out of the bubbles 480, as indicated by the arrow 486, such as by diffusion or exchange, it contributes to the reaction mixture 482. This behaviour can be referred to as auto-staging, and in accordance with the invention oxygenate is added to the reaction mixture more or less continuously at a plurality of locations along the feed trajectory.

To investigate this effect of bypassing in bubbles, the simple, isothermal, plug-flow reactor model used in Comparative Example 2 was modified to incorporate bypassing of a fraction of the feed gas. The reactor is divided into two zones: one in which a fraction of the gas, $f_e$, passes in plug-flow through the catalyst (emulsion zone); and a zone in which the remaining gas flows (also in plug flow) but where there is no catalyst (bubble zone). This bubble zone is in contact with the emulsion zone along the length of the reactor and there is continuous exchange of gaseous components between the two zones modelled by a variable mass transfer coefficient, $r_I$ (dimensionless). Only the gas passing through the catalyst undergoes reaction in the model.

In this way it is possible to examine the effect of bypassing by varying the degree of exchange of gas between the two zones through the parameter $r_I$ and by varying the fraction of gas $(1-f_e)$ bypassing the catalyst zone.

Results were generated for a catalyst amount of 5 tonnes for the reactor 411, 40 wt % of which being molecular sieve. A uniform temperature of 522° C. and pressure of 1 bar was assumed.

The composition of various streams indicated by the reference numerals of FIG. 4 are given in Table 3, wherein in this example $f_e$=0.5 and $r_I$=5.10$^6$ were selected.

TABLE 3

| Stream (kmol/h) | Recycle 438 | Feed 434 | Products 474 |
|---|---|---|---|
| DME | | 2744 | 0 |
| MeOH | | 1015 | 2 |
| H$_2$O | | | 3792 |
| C$_2^=$ | | | 887 |
| C$_3^=$ | | | 1558 |
| C$_4^=$ | 1021 | | 0 |
| C$_5^=$ | | | 10 |
| C$_6^=$ | | | 0 |
| C$_7^=$ | | | 0 |
| Total | 1021 | 3793 | 6249 |
| Total (t/h) | 57 | 159 | 159 |

Here the molar ratio of C2=/C3= is 0.57, significantly higher than in Comparative Example 2. It was found that in the limit of either high $r_I$ for any value of $f_e$, or $f_e$=1 (all gas flowing through catalyst), one obtains the same result as for the plug flow reactor. For lower values of $f_e$ and lower values of $r_I$ one can see that the effect of bypassing increases the selectivity to C2= significantly.

Reference is now made to FIG. 5, illustrating schematically an embodiment of a serial riser reactor system for carrying out the process according to the invention.

The reactor system 1 has three riser reactor stages 6,7,8 each having a single riser reactor 11,12,13, which riser reactors are serially arranged. Stage 6 with riser 11 is the first riser reactor stage, stage 7 with riser 12 is the second stage (riser), and stage 8 with riser 13 is the third stage (riser). Each riser has at its lower end an inlet end 16,17,18 with one or more inlets, and at its upper end an outlet end 21,22,23 with one or more outlets. The outlet 25 of the first riser 11 is connected via a conduit 28, such as a downer, to the inlet end 17 of the second riser 12. Likewise, outlet 29 of the second riser 12 is connected via a conduit 30 to the inlet end 18 of the third riser 13.

Each riser is moreover arranged to receive oxygenate at its inlet end, via conduits 34,35,36 which are all connected to oxygenate feedstock line 37. The first riser 11 has moreover an inlet for an olefinic co-feed from line 38, and an inlet for oxygenation catalyst via line 40. The feed lines 34,28 and 40 are shown to enter the inlet end 16 separately, but it will be understood that any two or all three feed lines can be combined before entering the inlet end 16.

To the effluent from riser 11, entering the inlet end 17 of the second riser 12 is added further oxygenation catalyst via line 41, wherein it will be understood that the catalyst can alternatively be added to the inlet end 17 directly. Likewise, oxygenation catalyst is added to the inlet end 18 of riser 13 via line 42.

The outlet from the last riser 13 is connected to a collector and vapour/solids separator unit 50 via line 51. The unit 50 can also be integrated with the outlet end of the last riser. It can be a large collector vessel combined with a plurality of cyclone separators, which can be internally housed in the collector vessel. The unit 50 has an outlet for vapour 52 and an outlet for catalyst 54, to which the catalyst feed lines 40,41,42 are connected. There is moreover provided a catalyst regeneration unit 60 which is arranged to receive catalyst via line 62 and returns regenerated catalyst to the unit 50 via line 64.

During normal operation of the reactor system 1, oxygenate, olefinic co-feed and oxygenation catalyst are fed via lines 34, 38, 40, respectively, to the inlet end 16 of the first riser 11 and form the reaction mixture of oxygenate and olefinic component. Conversion in the first riser 11 over the oxygenation catalyst forms an olefinic first reactor effluent comprising a gaseous product comprising olefins, and catalyst. Substantially the entire reactor effluent is fed in this example via line 28 to the inlet end 17 of the second riser 12, together with oxygenate from line 35 and additional catalyst via line 41. Although it is possible to also feed an olefinic co-feed to the second riser 12, this is not needed and not necessarily advantageous, since the effluent from reactor 11 already contains olefins.

Additional oxygenation catalyst is added via line 41. Thus, the mass flow rate (mass per unit of time) of oxygenate conversion catalyst in the second riser is higher than in the first riser reactor. As shown in the drawing, it is premixed with the reactor effluent in line 29, but can also directly be admitted to the inlet end 17. The cross-section of the second riser is larger than that of the first riser. A useful design rule is to choose the cross-section increase from one riser to the next such that the weight hourly space velocity remains substantially constant, i.e. not deviating more than 50% from that of the previous riser reactor. For cylindrical risers, the increase in cross-section can also be expressed as an increase in diameter.

The weight hourly space velocity is suitably chosen such that a desired conversion is achieved at the outlet of the reactor.

When the weight hourly space velocity is substantially constant, the time to flow through the riser is the same for risers of the same height (as they are shown in the example).

The conversion in the second riser 12 proceeds similar to that in the first riser 11, wherein the role of the olefinic co-feed as olefinic component is taken over by the olefinic product in the effluent from the first riser.

In one embodiment, each gaseous effluent from one of the riser reactors has an oxygenate concentration below 10 wt %, in particular below 5 wt %, preferably below 2 wt %, more preferably below 1 wt %, still more preferably below 0.1 wt %. In this way, substantially full conversion of oxygenate in each riser reactor is realized. This is particularly beneficial at the last reactor effluent, as otherwise unreacted oxygenate has to be separated from the effluent in a work-up section. Separating e.g. unreacted methanol from water formed in the process is an undesirable and costly step in an industrial process.

In one embodiment, each gaseous effluent from one of the riser reactor stages, or preferably from all riser reactors individually, has a concentration of C5+ olefins (pentenes and higher olefins) of below 10 wt %, preferably below 5 wt %, more preferably below 2 wt %, yet more preferably below 1 wt %, still more preferably below 0.1 wt %. In particular, the C5+ olefins can comprise at least 50 wt % pentenes, more in particular at least 80 wt %, even more in particular at least 90 wt % of pentenes. In particular the pentene concentration of the gaseous effluent can be below 10 wt %, preferably below 5 wt %, more preferably below 2 wt %, yet more preferably below 1 wt %, still more preferably below 0.1 wt %.

In this way the ratio of C5+ olefins (in particular C5 olefins) to oxygenate at the subsequent riser inlet to which oxygenate is added is kept minimum in the process. Without wishing to be bound to a particular hypothesis, it is currently believed that keeping the ratio C5+ olefins/oxygenate, in particular C5 olefins/oxygenate, small is beneficial to ethylene selectivity, more in particular in the case that the oxygenate comprises oxygen-bonded methyl groups. It is currently believed that pentenes should be preferentially cracked to yield ethylene and propylene, as opposed to alkylation to higher olefins by reaction with the oxygenate. Cracking of higher olefins is thought to result is a lower concentration of ethylene in the final product.

Effluent from the second riser 12 is fed to the inlet end 18 of the third riser 13, and combined with additional feeds of oxygenate via line 36 and oxygenation catalyst via line 42, in principle in the same way as discussed for the inlet end 17 of the second riser 12.

The cross section of the third riser 13 is again larger than that of the second riser. It can be preferred to design each riser and the respective catalyst throughput such that substantially full conversion of oxygenate is achieved in the riser, this can be most desirable for the last riser so that substantially no oxygenate forms part of the effluent from the last riser.

The effluent from the outlet end 23 of the last riser 13 comprises olefin-containing product and catalyst. The product is separated from the catalyst in the collection and vapour/solids separator unit 50.

Under typical operating conditions the deactivation of oxygenate catalyst, such as due to coking, occurs on a timescale much longer than the average contact time the riser reactors. In such circumstances it is not needed to regenerate all of the catalyst in the unit 50. It is rather sufficient then to only send a portion of the catalyst to the catalyst regeneration unit 60, where typically coke is burned partially or substantially fully at temperatures of about 600° C. or more. The size of the portion sent to the regeneration unit 60 depends on the average degree of deactivation or coking, and on the regeneration conditions, e.g. partial or full burning of coke.

It will be understood that it is also possible to arrange more vapour/solids separators, such as one for each outlet from a riser reactor. In the latter case, effluent from each riser reactor is separated into catalyst, and the vapour product from every riser reactor, except the last, is suitably fed to the subsequent riser reactor. Obviously a larger amount of oxygenation catalyst then needs to be added to the inlet end of the subsequent riser reactors. The separated catalyst can be collected in one or more shared collection vessels, and (full or partial) regeneration can occur in one or more shared regenerator units.

The olefin-containing product stream in line 52 is preferably at least partially recycled as olefinic co-feed to the inlet of the first reactor, line 38. Preferably this is done after one or more fractionation steps, to isolate an optimised olefinic co-feed composition from the olefin-containing product, and to obtain a desired product stream such as a stream or streams comprising predominantly ethylene and propylene. Preferred compositions of the olefinic co-feed have been discussed hereinbefore.

FIG. 5 shows schematically a separation system 70 for example including one or more distillation columns, fractionating the olefin-containing product stream 52 into a light fraction 73 comprising light contaminants, such as carbon monoxide, carbon dioxide, methane; a light olefinic product fraction 74 comprising for example ethylene and optionally propylene; a middle fraction 76 comprising e.g. C4 olefins; and one or more heavy product fractions, e.g. fractions with hydrocarbons with 5, 6 or 7+ hydrocarbons, in line 78. Also an outlet line 79 for withdrawing a water-rich fraction is provided. The middle fraction 76 can suitably be recycled to line 38.

EXAMPLE 4

As further example according to the present invention, model calculations for a reactor system comprising three sequential risers in a configuration according to FIG. 5 are presented. Reference numerals of FIG. 5 are used to designate the various system components and streams. The risers 11,12, 13 have equal height and increasing diameters. The oxygenate feed via line 34 to the first riser consists of 17.3 kmol/h dimethylether (DME), 6.1 kmol/h methanol (MeOH), and 0.4 kmol/h C4 paraffins. Further, an olefinic co-feed of 16.4 kmol/h C4 olefins and 7.8 kmol/h C4 paraffins is added via line 38. These data are also given in the columns for lines 34 and 38 in Table 4. 50910 kg/h of catalyst are fed through line 40. The catalyst was assumed to contain 40% of oxygenation zeolite.

The effluent from riser 11 in line 28 comprises, in addition to the catalyst, reaction products as shown for line 28 in Table 4. The entire effluent from riser 11, including the catalyst, is fed to the riser 12. Additional oxygenate feed is added via line 35, as shown in Table 4, and 25760 kg/hr catalyst is added via line 41.

The effluent from riser 12 in line 30 comprises, in addition to the catalyst, reaction products as shown for line 30 in Table 4. The entire effluent from riser 12, including the catalyst, is fed to the riser 13. Additional oxygenate feed is added via line 36, as shown in Table 4, and 48920 kg/hr catalyst is added via line 42.

In the calculations, moreover the temperature profile along the reactors and the pressure distribution was taken into account.

The composition of the reaction product in line 51 is also shown in Table 4. All of the olefinic co-feed 38 is obtained as a fraction from the reaction product. From the ethylene and propylene concentration in the reaction product, a high molar ratio of ethylene to propylene of 0.82 can be calculated. Also with this more extended model, a high selectivity of the reaction towards ethylene, for example when compared to Example 1, is observed.

Table 4 only shows the main components of the reactor effluents. Table 5 lists the concentrations of minor by-products not listed in Table 4 in the effluent 51, totaling about 12 wt % of the reaction product.

TABLE 4

| | Line | | | | | | |
|---|---|---|---|---|---|---|---|
| | 38 | 34 | 28 (excl. cat.) | 35 | 30 (excl. cat.) | 36 | 51 (excl. cat.) |
| DME | 0 | 17 | 0 | 17 | 0 | 17 | 0 |
| MeOH | 0 | 6 | 0 | 6 | 0 | 6 | 0 |
| H2O | 0 | | 23 | | 47 | | 70 |
| C2= | 0 | | 7 | | 14 | | 21 |
| C3= | 0 | | 19 | | 22 | | 26 |
| C4= | 16 | | 9 | | 13 | | 17 |
| C4,0 | 8 | 0 | 8 | 0 | 8 | 0 | 8 |
| C5= | 0 | | 0 | | 0 | | 0 |
| C6= | 0 | | 0 | | 0 | | 0 |
| C7= | 0 | | 0 | | 0 | | 0 |
| T (C.) | 522 | 341 | 528 | 293 | 531 | 52 | 528 |

TABLE 5

| By-products | kmol/h |
|---|---|
| CO + CO2 | 0.4 |
| C1 | 0.8 |
| other C2 species | 0.1 |
| other C3 species | 1.0 |
| other C4 species | 0.4 |
| other C5 species | 0.9 |
| other C6+ species | 0.5 |

Examples of an oxygenate that can be used as feedstock in the present invention include alcohols, such as methanol, ethanol, isopropanol, ethylene glycol, propylene glycol; ketones, such as acetone and methylethylketone; aldehydes, such as formaldehyde, acetaldehyde and propionaldehyde; ethers, such as dimethylether, diethylether, methylethylether, tetrahydrofuran and dioxane; epoxides such as ethylene oxide and propylene oxide; and acids, such as acetic acid, propionic acid, formic acid and butyric acid. Further examples are dialkyl carbonates such as dimethyl carbonate or alkyl esters of carboxylic acids such as methyl formate. Of these examples, alcohols and ethers are preferred.

Examples of preferred oxygenates include alcohols, such as methanol, ethanol, isopropanol, ethylene glycol, propylene glycol; and dialkyl ethers, such as dimethylether, diethylether, methylethylether. Cyclic ethers such as tetrahydrofuran and dioxane, are also suitable.

The oxygenate used in the process according to the invention is preferably an oxygenate which comprises at least one oxygen-bonded alkyl group. The alkyl group preferably is a C1-C4 alkyl group, i.e. comprises 1 to 4 carbon atoms; more preferably the alkyl group comprises 1 or 2 carbon atoms and most preferably one carbon atom. The oxygenate can comprise one or more of such oxygen-bonded C1-C4 alkyl groups. Preferably, the oxygenate comprises one or two oxygen-bonded C1-C4 alkyl groups.

More preferably an oxygenate is used having at least one C1 or C2 alkyl group, still more preferably at least one C1 alkyl group.

Preferably the oxygenate is chosen from the group of alkanols and dialkyl ethers consisting of dimethylether, diethylether, methylethylether, methanol, ethanol and isopropanol, and mixtures thereof.

Most preferably the oxygenate is methanol or dimethylether.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

By an olefin-containing product is understood a product consisting of or comprising an olefin. By an olefin is understood an organic compound containing at least two carbon atoms connected by a double bond. The product can comprise a mixture of different olefins. The product can be a mixture further comprising other one or more other hydrocarbonaceous and non-hydrocarbonaceous components, such as saturates, aromatic compounds, oxygenates, water, carbon monoxide, carbon dioxide.

In the present invention, oxygenate is contacted with an oxygenate conversion catalyst.

By an oxygenate conversion catalyst is understood a catalyst that is able to convert oxygenate into olefin. Any catalyst known to be able to convert oxygenate into olefin under suitable conditions may be used. Examples include catalysts comprising a molecular sieve, for example silico-alumino phosphates such as SAPO-34 (CHA type), and zeolite catalysts such as ZSM-22, ZSM-23, and ZSM-5.

The expression 'molecular sieve' is used in the description and claims for a material containing small regular pores and/or channels and exhibiting catalytic activity in the conversion of oxygenate to olefin. The molecular sieve can in particular be a zeolite. A zeolite is understood to be an aluminosilicate molecular sieve. Where reference is made in the description and in the claims to a molecular sieve, this can in particular be a zeolite.

Molecular sieve and zeolite types are for example defined in Ch. Baerlocher and L. B. McCusker, Database of Zeolite Structures: http://www.iza-structure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher).

The oxygenate conversion catalyst can be a zeolite catalyst. By a zeolite catalyst is understood a catalyst consisting of or containing a zeolite. Reference herein to zeolite is to a pure zeolite or to the zeolite portion of a catalyst containing other components as well.

Preferably, at least part of the molecular sieve is a molecular sieve comprising a 10-membered ring channel.

More preferably this molecular sieve is a molecular sieve having one-dimensional 10-membered ring channels. A molecular sieve having one-dimensional 10-membered ring channels is understood to be a molecular sieve having only 10-membered ring channels in one direction which are not intersected by other 8, 10 or 12-membered ring channels from another direction.

Preferably, the oxygenation catalyst comprises a molecular sieve selected from the group of TON-type (for example zeolite ZSM-22), MTT-type (for example zeolite ZSM-23), STF-type (for example SSZ-35), SFF-type (for example SSZ-44), EUO-type (for example ZSM-50), and EU-2-type molecular sieves or mixtures thereof.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., ZSM-48.

In a further preferred embodiment a molecular sieve of the MTT-type, such as ZSM-23, and/or a TON-type, such as ZSM-22 is used.

In a special embodiment the oxygenate conversion catalyst comprises, in addition to molecular sieve having one-dimensional 10-membered ring channels, at least 1 wt %, based on total molecular sieve in the oxygenate conversion catalyst, of a further molecular sieve having more-dimensional channels, in particular at least 5 wt %, more in particular at least 8 wt %. The presence of a minority portion of a more-dimensional molecular sieve in the oxygenate conversion catalyst was found to improve stability (slower deactivation during extended runs) and hydrothermal stability. Without wishing to be bound by a particular hypothesis or theory, it is presently believed that this is due to the possibility for converting larger molecules by the more-dimensional molecular sieve, that were produced by the 1-dimensional molecular sieve, and which would otherwise form coke. The further molecular sieve can for example be a MFI-type molecular sieve such as ZSM-5, or a SAPO-type molecular sieve such as SAPO-34. The weight ratio between the molecular sieve having one-dimensional 10-membered ring channels, and the further molecular sieve having more-dimensional channels can be in the range of from 1:1 to 100:1.

Preferably the further molecular sieve is a MFI-type molecular sieve, in particular zeolite ZSM-5, having a Silica-to-Alumina ratio SAR of at least 60, more preferably at least 80, even more preferably at least 100, yet more preferably at least 150. At higher SAR the percentage of C4 saturates in the C4 totals produced is minimized. In special embodiments the oxygenate conversion catalyst can comprise less than 35 wt % of the further molecular sieve, based on the total molecular sieve in the oxygenate conversion catalyst, in particular less than 20 wt %, more in particular less than 18 wt %, still more in particular less than 15 wt %.

The preferred zeolites used in the present invention are distinct from zeolites having small pore 8-ring channels or zeolites having large pore 12-ring channels.

In one embodiment, molecular sieves (zeolites) in the hydrogen form are used, e.g., HZSM-22, HZSM-23, HZSM-48, HZSM-5. Preferably at least 50% w/w, more preferably at least 90% w/w, still more preferably at least 95% w/w and most preferably 100% of the total amount of molecular sieve used is in the hydrogen form, based on total molecular sieve in the oxygenate conversion catalyst. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 500° C. for 1 hour or more. The molecular sieves obtained after ion-exchange are also referred to as being in the ammonium form. Preferably the zeolite has a silica to alumina ratio (SAR) in the range from 1 to 1000. The SAR is defined as the molar ratio of $SiO_2/Al_2O_3$ corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, a SAR in the range of 20-120 is preferred, in particular in the range of 30-80. Good performance in terms of activity and selectivity has been observed with a SAR of about 50.

For ZSM-5, a SAR of 60 or higher is preferred, in particular 80 or higher, more preferably 100 or higher, still more preferably 150 or higher, such as 200 or higher.

The molecular sieve can be used as such or in a formulation, such as in a mixture or combination with a so-called binder material, e.g. silicabinder, aluminabinder, silica-alumina binder, zirconiabinder, and/or a filler material, e.g. kaolin, kaolinit, attapulgite, montmorillonite, bentonite, alumina, silica, titania, and optionally also with an active matrix component. Other components can also be present in the formulation. Typically, molecular sieve content, such as in particular zeolite content, in a formulated catalyst is in the range of from 1 wt % to 50 wt %, preferably 10 to 40 wt %, more preferably 20 to 40 wt %, based on total formulated catalyst.

If one or more molecular sieves are used as such, in particular when no binder, filler, or active matrix material is used, the molecular sieve(s) itself is/are referred to as oxygenate conversion catalyst. In a formulation, the molecular sieve(s) in combination with the other components of the mixture such as binder and/or filler material is/are referred to as oxygenate conversion catalyst.

It is desirable to provide a oxygenate conversion catalyst having good mechanical or crush strength, because in an industrial environment the catalyst is often subjected to rough handling which tends to break down the catalyst into powder-like material. The latter causes problems in the processing, such as attrition of catalyst particles in a riser reactor. Preferably the molecular sieve is therefore incorporated in a binder material. Examples of suitable materials in a formulation include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used.

By serially arranged riser reactors is understood that at least part of the riser reactor effluent of a preceding riser reactor is fed into a subsequent riser reactor, which subsequent riser reactor is connected directly or indirectly with the first riser reactor via one or more conduits.

By an olefinic composition or stream, such as an olefinic product, product fraction, fraction, effluent, reaction effluent or the like is understood a composition or stream comprising one or more olefins, unless specifically indicated otherwise. Other species can be present as well. The olefinic composition or stream can comprise one type of olefin or a mixture of olefins.

By an olefin is understood an organic compound containing at least two carbon atoms connected by a double bond.

In particular the olefinic co-feed can contain a mixture of olefins. Apart from olefins, the olefinic co-feed may contain other hydrocarbon compounds, such as for example paraffinic compounds. Preferably the olefinic co-feed comprises an olefinic portion of more than 50 wt %, more preferably more than 60 wt %, still more preferably more than 70 wt %, which olefinic portion consists of olefin(s). The olefinic co-feed can also consist essentially of olefin(s).

Any non-olefinic compounds in the olefinic co-feed are preferably paraffinic compounds. Such paraffinic compounds are preferably present in an amount in the range from 0 to 50 wt %, more preferably in the range from 0 to 40 wt %, still more preferably in the range from 0 to 30 wt %.

The olefin can be a mono-olefin, having one double bond, or a poly-olefin, having two or more double bonds.

Preferably olefins present in the olefinic co-feed are mono-olefins. C4 olefins, also referred to as butenes (1-butene, 2-butene, iso-butene, and/or butadiene), in particular C4 mono-olefins, are preferred components in the olefinic co-feed. Preferably the olefinic portion of the olefinic co-feed, and of the recycle stream, comprises at least 90 wt % of C4 olefins, more preferably at least 99 wt %. Butenes as co-feed have been found to be particularly beneficial for high ethylene selectivity.

The olefinic co-feed can also comprise propylene. Recycling part or all of the propylene may be an interesting option for maximising ethylene selectivity of the overall process, but when it is desired to maximise ethylene+propylene yield, it is not preferred to recycle propylene. Preferably substantially no ethylene (i.e. less than 5 wt %, preferably less than 1 wt %, of the ethylene in the overall reaction product, based on ethylene) is recycled.

Preferably the reaction product containing one or more olefins is separated into one or more fractions, preferably at least a product fraction containing olefins intended as a product and a further fraction. Preferably at least part of the further fraction is recycled to the start of the process as (all or part of) the olefinic co-feed. The product fraction can be a lighter fraction than the recycle fraction, and there can also be one or more further fractions heavier than the recycle fraction. The product fraction can for example mainly comprise ethylene and propylene, the recycle fraction mainly butylenes, and the further fraction mainly C5+ olefins.

The olefinic co-feed preferably consists, during normal operation, for at least 50 wt %, more preferably at least 80 wt %, still more preferably from 90 to 100 wt % of such a recycle fraction of the reaction product. In a specifically preferred embodiment the olefinic co-feed consists essentially of a recycle fraction of the reaction product. If that is not the case, part of the olefinic co-feed can originate from an external source, in particular during start-up when no or insufficient olefinic reaction products are available.

One particularly suitable recycle stream consists essentially, i.e. for at least 99 wt %, of 1-butene, 2-butene (cis and trans), isobutene, n-butane, isobutene, butadiene. The skilled artisan knows how to obtain such a fractions from the olefinic reaction effluent such as by distillation.

The process can be conducted in any reactor system known to the skilled person and may for example contain a fixed bed, moving bed, fluidized bed, riser reactor and the like. A riser reactor system is preferred, in particular a riser reactor system comprising a plurality of serially arranged riser reactors.

Preferably reaction product containing one or more olefins is separated into one or more fractions, preferably at least a product fraction containing olefins intended as a product and a further fraction. Preferably at least part of the further fraction is recycled to the start of the process as (all or part of) the olefinic co-feed. The product fraction can be a lighter fraction than the recycle fraction, and there can also be one or more further fractions heavier than the recycle fraction. The product fraction can for example mainly comprise ethylene and propylene, the recycle fraction mainly butylenes, and the further fraction mainly C5+ olefins.

The olefinic co-feed preferably consists, during normal operation, for at least 50 wt %, more preferably at least 80 wt %, still more preferably from 90 to 100 wt % of such a recycle fraction of the reaction product. In a specifically preferred embodiment the olefinic co-feed consists essentially of a recycle fraction of the reaction product. If that is not the case, part of the olefinic co-feed can originate from an external source, in particular during start-up when no or insufficient olefinic reaction products are available. Preferably, at least 70 wt % of the olefinic feedstock in step a) of the process, during normal operation, is formed by a recycle stream obtained from fractionation of a riser reactor effluent, preferably at least 90 wt %, more preferably at least 99 wt %, and most preferably the olefinic feedstock is during normal operation formed by the recycle stream. In a preferred embodiment of a process with olefinic co-feed, the olefinic feedstock comprises at least 50 wt % of C4 olefins, and at least a total of 70 wt % of C4 hydrocarbon species. It is believed that this increases ethylene selectivity.

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range from 5:2 to 1:10 and more preferably in the range of 2:1 to 1:4. Most preferably the molar ratio in such a case is in the range of 1.5:1 to 1:3.

In addition to the oxygenate, and the olefinic co-feed, a diluent may be fed into the first riser reactor and/or any subsequent riser reactor. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range from 0.01 to 10 kg steam per kg oxygenate feed. Preferably the diluent, in particular steam, is less than 50 vol %, more preferably less than 30 vol %, of the total feedstock to the process, in particular less than 50 vol %, preferably less than 30 vol %, based on the total of oxygenate and diluent feed to the process.

The process can be carried out over a wide range of temperatures and pressures. Preferably, however, the hydrocarbon feed is contacted with the oxygenate conversion catalyst at a temperature in the range from 200° C. to 650° C. In a further preferred embodiment the temperature is in the range from 250° C. to 600° C., more preferably in the range from 300° C. to 550° C., most preferably in the range from 450° C. to 550° C.

In the presence of a molecular sieve having one-dimensional 10-membered ring channels the oxygenate conversion reaction is preferably conducted at a temperature of more than 450° C., preferably at a temperature of 460° C. or higher, in particular 480° C. or higher, more preferably at a temperature of 490° C. or higher. At higher temperatures a higher activity and ethylene selectivity is observed. One-dimensional molecular sieves having 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

The pressure can vary widely, preferably a pressure in the range from 1 to 8 bar is applied, more preferably a pressure in the range of 1 to 5 bar is applied.

To illustrate the difference in catalytic performance of ZSM-23 (a molecular sieve having one-dimensional 10-membered ring channels) and SAPO-34 in the present process, comparative experiments were performed under oxygenate conversion conditions as well as for the cracking of C5 olefins. SAPO-34 comprises small channels of 8-membered rings.

In FIGS. 6 and 7 the cracking of C5= olefins was studied in the temperature range of 440 to 480° C. over SAPO-34 (FIG. 6) and ZSM-23 (FIG. 7). 2-methyl-2-butene (4 vol. % in inert gas) was cracked at various temperatures with a GHSV of 50,000 ml·g$^{-1}$·h$^{-1}$. Comparing the performance of the two catalysts a clear distinction is observed: cracking 2-methyl-2-butene over ZSM-23 results in high selectivity to ethylene and propylene with good activity. In contrast to ZSM-23, SAPO-34 displays a much lower activity in cracking C5=, which is likely due to pore size limitations. Furthermore, SAPO-34 also appeared to deactivate as the cracking activity decreased while the temperature was increased. ZSM-23 on the other hand shows increasing cracking activity with increasing temperature, which continues to higher temperatures than used for this comparison.

FIGS. 8 and 9 show product distribution in time when reacting a mixture of 1-butene (vol %) and DME (vol %) in an inert gas as feed over SAPO-34 (FIG. 8) and ZSM-23 (FIG. 9) at 525° C. and a GHSV of 30,000 ml·g$^{-1}$·h$^{-1}$. Clearly, SAPO-34 deactivates much faster when compared to ZSM-23 in this case of oxygenate conversion with butene co-feed.

What is claimed is:

1. A process for the preparation of an olefinic product, which process comprises contacting a reaction mixture comprising an oxygenate feedstock and an olefinic component with an oxygenate conversion catalyst comprising a molecular sieve having one-dimensional 10-membered ring channels, in a flow-through reactor unit defining a flow trajectory for fluids towards a downstream outlet for an olefinic reaction effluent from the flow-through reactor unit, wherein an olefinic co-feed is added at an upstream olefin feed inlet of the flow-through reactor unit, wherein oxygenate feedstock is admitted to the reactor such that it is added to the reaction mixture at a plurality of locations along the feed trajectory and wherein the cross-sectional area of the reactor system increases in the direction of flow.

2. The process according to claim 1, wherein for a selected position along the flow trajectory an oxygenate-to-olefin ratio is kept below a predetermined threshold, which threshold is lower than for the case that all oxygenate would be admitted at the upstream feed inlet.

3. The process according to claim 2, wherein the oxygenate-to-olefin ratio is related to a molar ratio of oxygen-bonded alkyl groups to olefin double bonds.

4. The process according to claim 1, wherein the oxygenate conversion catalyst is flowing through the reactor as well, and wherein oxygenate conversion catalyst is admitted to the reactor at multiple locations along the flow trajectory.

5. The process according to claim 1, wherein the flow-through reactor comprises a plurality of sequential reaction zones.

6. The process according to claim 1, wherein the flow-through reactor unit comprises a riser reactor.

7. The process according to claim 1, wherein the flow-through reactor unit comprises a fluidized bed reactor.

8. The process according to claim 7, wherein the oxygenate feedstock is allowed to enter the reactor system at an upstream oxygenate inlet, and wherein the flow properties of the oxygenate feedstock are adjusted such that oxygenate feedstock containing bubbles progress along the flow trajectory, adding oxygenate to the reaction mixture by exchange and/or diffusion along the way.

9. The process according to claim 1, wherein the oxygenate feedstock comprises oxygenate species having an oxygen-bonded alkyl group.

10. The process according to claim 1, wherein at least part of the olefinic feedstock is obtained from recycling part of the olefinic reaction effluent.

11. The process according to claim 1, wherein the one-dimensional molecular sieve having 10-membered ring channels comprises at least one of a molecular sieve of the MTT-type and/or of the TON-type.

12. The process according to claim 1, wherein the oxygenate conversion catalyst comprises at least 50 wt %, based on total molecular sieve in the oxygenate conversion catalyst, of the one-dimensional molecular sieve having 10-membered ring channels.

13. The process according to claim 1, wherein the reaction mixture is contacted with the oxygenate conversion catalyst to react at a temperature of more than 470° C.

14. The process according to claim 1, wherein the olefinic product comprises 50 mol % or more of ethylene and/or propylene, based on total hydrocarbons in the olefinic product.

* * * * *